United States Patent [19]

Chimienti

[11] Patent Number: 5,090,564
[45] Date of Patent: Feb. 25, 1992

[54] PROTECTIVE CONTAINER FOR A NEEDLE

[76] Inventor: Vincent J. Chimienti, 2 Osborne La., Greenvale, N.Y. 11548

[21] Appl. No.: 646,660

[22] Filed: Jan. 25, 1991

[51] Int. Cl.⁵ ............................................. B65D 85/20
[52] U.S. Cl. ................................. 206/365; 206/477; 220/4.23; 220/908
[58] Field of Search .................. 220/4.21, 4.22, 4.23, 220/4.24, 4.25, 908; 206/363, 364, 365, 366, 477, 480, 564, 565

[56] References Cited

U.S. PATENT DOCUMENTS

| | | | |
|---|---|---|---|
| 600,002 | 3/1898 | Havell | 206/366 |
| 1,059,285 | 4/1913 | Dickinson | 206/365 X |
| 1,239,308 | 9/1917 | Scott | 206/366 |
| 2,651,407 | 9/1953 | Blackman | 206/366 |
| 2,798,784 | 7/1957 | Marshall | 220/4.22 X |
| 3,255,873 | 6/1966 | Speelman | 206/366 |
| 3,494,458 | 2/1970 | Meierhoefer | 206/366 |
| 3,642,123 | 2/1972 | Knox | 206/365 |
| 3,727,749 | 4/1973 | Martin | 206/366 |
| 3,768,635 | 10/1973 | Eggert | 206/366 |
| 3,876,067 | 4/1975 | Schwarz | 206/366 X |
| 4,596,562 | 6/1986 | Vernon | 206/366 X |
| 4,753,345 | 6/1988 | Goodser et al. | 206/365 X |
| 4,846,803 | 7/1989 | Emerson | 206/365 X |
| 4,890,731 | 1/1990 | Mroz | 220/4.24 X |
| 4,921,096 | 5/1990 | McFarlane | 206/365 X |
| 4,973,315 | 11/1990 | Sincock | 206/365 X |

Primary Examiner—David T. Fidei
Assistant Examiner—Jacob K. Ackun, Jr.
Attorney, Agent, or Firm—Collard, Roe & Galgano

[57] ABSTRACT

A disposable hypodermic needle sheath and remover which is designed as a disposable two-part container, having two halves. The container can be placed in an open position and a used needle placed into its ribs. The ribs have needle receiving grooves or channels which are disposed within the container and will snugly grasp the needle when the container is closed. The needle sheath and remover permits a needle to be covered immediately after use due to its portability, thus reducing the likelihood that the used needle will cause injury.

7 Claims, 1 Drawing Sheet

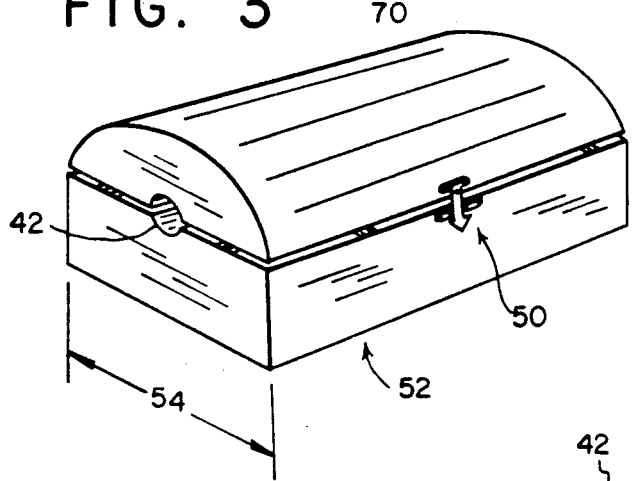
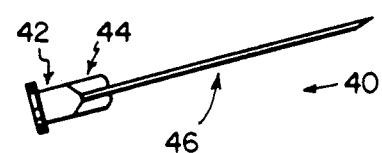
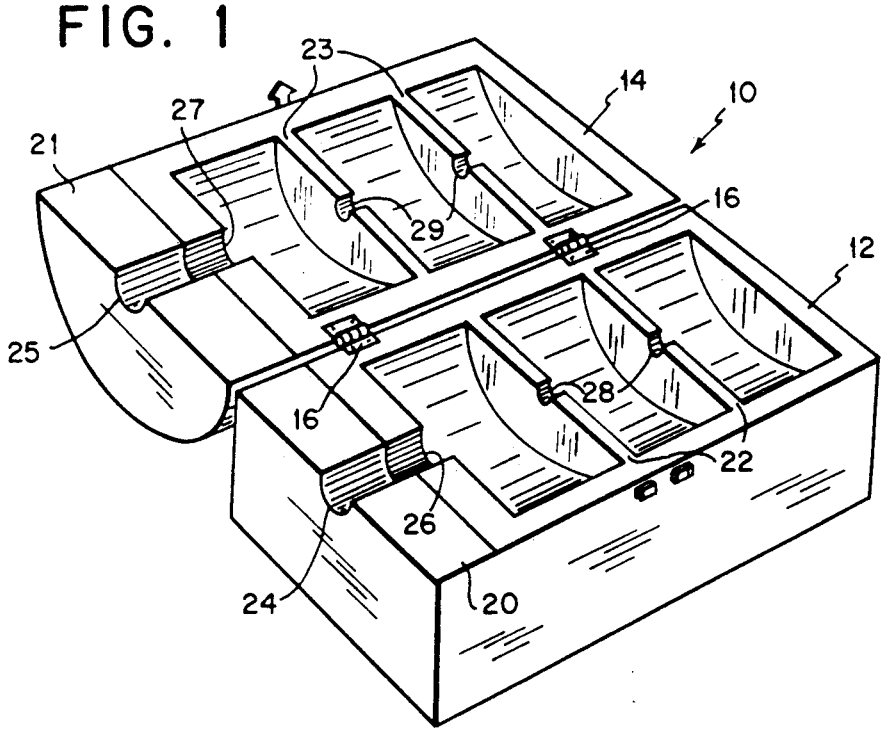
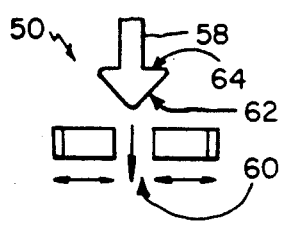
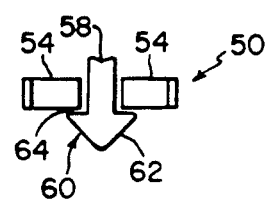

PROTECTIVE CONTAINER FOR A NEEDLE

BACKGROUND OF THE INVENTION

1. Field of the Invention

The invention relates to a protective container for a disposable hypodermic syringe and needle combination, more particularly to a hypodermic needle sheath and remover that allows the safe covering, removal and disposal of the needle to prevent accidental injury to patients and medical professionals.

2. Description of the Prior Art

Various types of syringe assemblies for receiving and dispensing medication as well as other materials have been known. In general, the medication or other materials are introduced into the hollow barrel portion either by receiving the same through the needle which communicates with the barrel interior, or by means of a frangible container, such as an ampule, which is placed within the hollow barrel. Applying pressure to the plunger causes the medication or other material to be expressed through the hollow needle.

Other assemblies also utilize needles to draw blood or set up an intra-venous catheter. In both cases, a used needle must be properly disposed of. In a situation where blood is drawn, the needle must be separated from the syringe before the syringe can be sent to the lab. In other words, most labs will not accept the blood sample if a needle is attached.

These various assemblies are often used for patients suffering from infectious diseases. Therefore, it has been considered of great importance in the art to avoid accidents, where doctors, nurses, or other persons suffer accidental puncture wounds from use of needles. Presently, the safe disposal of used syringes and needles is considered a serious problem in the art, particularly in light of the recent spread of acquired immune deficiency syndrome (AIDS) and hepatitis, and the widespread abuse of syringes and needles by addicts for administering illicit drugs.

In order to prevent the incidence of puncture wounds which are sometimes accidentally self-inflicted by doctors, nurses and hospital housekeeping staff, there has been a need to provide a simple method for immediately covering the hypodermic needle after use.

U.S. Pat. Nos. 4,702,738 and 4,908,023 address this problem by providing a disposable hypodermic syringe with a retractable and lockable sheath. Other patents, such as U.S. Pat. No. 4,356,822, also disclose a syringe assembly having a sheath which can be extended to cover the needle but which cannot be locked in this extended position. In addition, U.S. Pat. Nos. 3,967,621, 4,139,009, 4,237,882, 4,416,663, 4,573,972, 4,573,975, 4,731,059, 4,139,009 and 4,966,591 all disclose syringe assemblies with various means for protecting the needle either before or after use.

Another device is known which has a base that attaches to the syringe in between the syringe and the needle. A plastic connector holds a cover which dangles from the base and is meant to snap over the needle after use. This device impedes the use of the needle however. In addition, none of these patents permits the needle to be safely covered and safely removed from a syringe and disposed.

Some health facilities provide a sharps container for disposal of used needles. These containers may be equipped with a lever which carries a blade to cut needles from syringes before disposal. Other needle assemblies are disposed of without destruction.

This system has a major disadvantage. Although the patient and health professional are safe once an item has reached the sharps container, those containers still need to be emptied and the waste disposed of. Exposed needles also represent a danger to personnel who have to empty the sharps containers.

These sharps containers are typically wall-mounted. Frequently, after a needle is used, the health professional will place the used needle on the bed or on a nearby table in order to continue to attend to the patient. When an opportunity arises, the health professional will then dispose of the needles. This can be dangerous for the patient, the attendant health professional, and other health professionals. In addition, the needles must still be transported to the sharps container. This presents the risk of possible injury if the person carrying them trips, falls or accidentally sticks someone.

SUMMARY OF THE INVENTION

Accordingly, it is an object of the present invention to provide a hypodermic needle sheath and remover wherein any type of needle can be safely covered.

It is another object of the invention to provide a hypodermic needle sheath and remover wherein a needle can be safely removed from a syringe.

It is yet a further object of the present invention to provide such a hypodermic needle sheath and remover which is adapted for use in accordance with standard accepted medical procedures.

Accordingly, these and other objects are achieved by a hypodermic needle sheath and remover of the type which is discardable after a single use, along with the used needle.

The sheath is a container with two sections which is generally cylindrical in shape. Each section extends to the ends of the cylinder, but encompasses only half of the circumference. When the sheath is in the open position, it can conveniently fit in the palm and provides a large surface area for the needle to hit.

Ideally, the cross-section of the cylinder would be somewhat oval with the line separating the two sections, traversing the widest part of the oval.

Most needle covers which permit removal of the needle from the syringe, accept the needle from its pointed end. As can be appreciated, this results in needle pricks by even the most careful health professionals due to the time constraints frequently associated with medical procedures. With the invention, the surface area is so large compared to the point of the needle that a significant margin of error is provided for the health professional.

Conveniently, one of the sections can have a squared-off bottom, so that it can rest flatly on a table top. This provides an even greater margin of error, since the palm isn't even under the sheath.

The sheath is also conveniently provided with a receiving groove which is configured and designed to securely grasp the base of the needle. Thus, when the sheath is closed, the needle will be firmly held and prevented from rotating. At this point, the needle can be safely removed from any apparatus to which it is connected.

Ideally, one of the sections is provided with a locking pin and the other section with a receiving port. Thus, when the sheath is fully closed, the locking pin is introduced into the receiving port, providing a locking means.

Conveniently, the sheath is provided as a portable unit. In this sense it is much more effective than current Sharps containers, which are typically fixably mounted to a wall. After that a needle has been used and before it is disposed in the Sharps container, it represents a constant risk to the patient, as well as health professional. As can be appreciated, having a sheath readily available would provide for immediate covering and render the needle harmless. Also, the health professional need not walk any distance with the exposed used needles.

In an additional embodiment of the invention, the sheath is attached to the needle or other apparatus by a thin string, e.g., a thin piece of plastic. It the string and sheath impede use of the needle, the string can simply be broken. In this way, it is insured that a sheath always accompanies a needle.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 1 is a perspective view thereof;

FIG. 2 is a perspective view of a hypodermic needle;

FIG. 3 is another perspective view of the protective device in the closed position thereof; and, FIGS. 4a and 4b are side elevational views of the locking mechanism.

DETAILED DESCRIPTION OF THE PREFERRED EMBODIMENTS

Referring now in detail to the drawings and, in particular FIG. 1, there is illustrated a protective device 10 for a needle 40 embodying the present invention. Protective device 10, shown in the open position, has two similar halves shown as bottom rectangular end section 12 and top semi-oval end section 14. The sections are secured to each other along adjacent sides by a set of hinges 16. The length of device 10 is designed to be longer than any of the available needles that it is to accommodate, so that the end of the needle shaft will not protrude past end sections 12 and 14.

The hollow bodies of sections 12 and 14 contain end ribs 20 and 21 and a set of central ribs 22 and 23. End ribs 20 and 21 each contain a two-part depression shown as smooth channels 24 and 25 and ribbed channels 26 and 27. Also, central ribs 22 and 23 each have notches 28 and 29.

As shown in FIG. 2, needle 40 has three sections, namely, smooth section 42 having an end flange, a ribbed section 44, and a shaft 46. Smooth channels 24 and 25 are configured and designed to snugly receive smooth section 42. Ribbed channels 26 and 27 (from FIG. 1) are configured and designed to engagingly receive ribbed section 44. Notches 28 and 29 (from FIG. 1) are configured and designed to accept shaft 46. Once protective device 10 is closed (shown in FIG. 3), ribbed channels 26 and 27 frictionally engage ribbed section 44 and prevent rotation thereof. This allows needle 40 to be readily unscrewed or released from the syringe while it is captured inside device 10. Once the needle is removed from the syringe, smooth channels 24 and 25 provide sufficient frictional engagement with smooth section 42 to prevent needle 40 from accidentally sliding out of protective device 10. The flange of smooth section 42 will protrude slightly from the end of protective device 10.

When the protective device 10 is in its closed position, a look 50 is engaged to prevent its re-opening, and removal of needle 40.

Protective device 10 is conveniently provided with a rectangular bottom surface 52, since the outer, oval portion of protective device 10 would render it unstable were it placed on a flat surface. Protective device 10 can be placed on a table or tray near the patient until it is required. Also, the health professional need not have a hand underneath the device at all if it is resting on a flat surface.

In the event that a flat surface is not available, protective device 10 can be held in the palm of the hand. The overall shape of the device can be fully oval, fully rectangular, or semi-oval and semi-rectangular. The total width provided by the open protective device 10 is designated as twice width 54.

FIGS. 4a and 4b show lock 50 in greater detail Referring to FIG. 4a, a pin 58 can be provided for top section 14, for example. A receiving port 60 can be provided for bottom section 12, for example. As top section 14 is brought toward the closed position, a tapered portion 62 of locking pin 58 aligns with receiving port 60 to guide locking pin 58. The fully closed position is defined by locking pin 58 being fully received within the locking port, as seen in FIG. 4b. A wide portion 64 is below the receiving port and does not permit the reopening of the protective device.

In keeping with accepted medical procedures, the protective device 10 could be used in the following manner, for example.

To administer medication, the medical professional would choose an appropriately sized needle and syringe assembly which would be filled with the medication. The needle and syringe assembly along with protective device 10 would be taken to the patient and the medication would be administered. Protective device 10 could be held in the hand, placed nearby on the bed or placed nearby on a table. As soon as the needle is removed from the patient, it can be placed into protective device 10 and rendered harmless. The medical professional need not get up or leave the patient's side in order to utilize the protective device. This can be extremely important where the patient needs supervision immediately following administration of the medication.

A similar procedure can be followed when setting up an intravenous catheter. In this situation, the patient always requires continued supervision after the needle is removed, i.e., the catheter must be set up. With the invention, the medical professional can render the needle harmless immediately after use without leaving the patient. Again, this prevents the needle from being placed down where it can cause injury.

Since the connecting portion of all needles (see FIG. 2, smooth section 42) is the same, protective device 10 can be universal in further keeping with accepted medical practice That is, the barrels of all syringes are the same, therefore, the connecting portions of all needles are the same. Also, winged blood collection sets and other types of needles could be placed inside the needle container, as long as their length is less than that of the needle container.

Needle container or sheath 10 is preferably constructed of a non-breakable plastic material and is designed to be inexpensive and disposable after each use. The outer portion may optionally be provided with molded ribs (70) to aid in gripping. Needle sheath 10 may optionally include a string which attaches needle sheath 10 to needle 40. In this manner, it is ensured that each needle is accompanied by a protective container.

Accordingly, while only a single embodiment of the present invention has been shown and described, it is obvious that many changes and modifications may be made thereunto without departing from the spirit and scope of the invention.

What is claimed is:

1. A disposable needle sheath for receiving, containing, and disposing of a used hypodermic needle comprising:
   a needle container which has two substantially similar halves which are flexibly connected so as to permit orientation of the halves in an open position and a non-releasably closed position, and
   a set of ribs, disposed within said needle container, including centrally disposed channels for receiving the needle body in said open position and ridges lining said channels which are capable of gripping the surface of the needle body when said needle container is in said non-releasably closed position, whereby when said container halves are non-releasably closed around a needle on a syringe, said needle sheath receives and frictionally retains the needle, thereby allowing the needle to be safely twisted off a syringe and disposed of along with the needle sheath.

2. The needle sheath as claimed in claim 1, wherein said needle container further includes locking means, disposed on the container halves, which engage the closed position and prevent return to the open position.

3. The needle sheath as claimed in claim 2, wherein said locking means further comprises:
   a locking pin located on one half of said needle container, and
   a receiving port located on the other half of said needle container, for receiving said locking pin in the closed position and permanently preventing its return to the open position.

4. The needle sheath as claimed in claim 1, wherein one of said needle containers has a flat outer portion for stable placement on a surface.

5. The needle sheath as claimed in claim 1, wherein said needle container has a semi-oval, semi-rectangular shape, the halves being divided along a line which transverses the widest part of said needle container, thereby presenting an enlarged surface area when open.

6. The needle sheath as claimed in claim 1, wherein the needle sheath includes a string for removable attachment to the needle.

7. The needle sheath as claimed in claim 1, wherein said needle sheath is provided with ribs along its outer surface.

* * * * *